United States Patent [19]

Joergensen

[11] Patent Number: 5,070,186

[45] Date of Patent: Dec. 3, 1991

[54] MAGNESIUM CONTAINING INSULIN SOLUTION

[75] Inventor: Klaus Joergensen, Virum, Denmark

[73] Assignee: Novo Industri A/S, Bagsvaerd, Denmark

[21] Appl. No.: 340,331

[22] Filed: Apr. 19, 1989

Related U.S. Application Data

[63] Continuation of Ser. No. 109,065, Oct. 16, 1987, abandoned.

[30] Foreign Application Priority Data

Oct. 20, 1986 [DK] Denmark ............................. 5033/86
Jul. 10, 1987 [DK] Denmark ............................. 3569/87

[51] Int. Cl.$^5$ ........................ C07K 7/40; A61K 37/26
[52] U.S. Cl. ................................... 530/304; 530/303; 530/305
[58] Field of Search ............... 514/3, 4; 530/303, 304, 530/305

[56] References Cited

U.S. PATENT DOCUMENTS

| | | | |
|---|---|---|---|
| 2,076,082 | 2/1936 | Hagedorn et al. | 514/4 |
| 2,179,384 | 4/1937 | Scott | 514/4 |
| 2,190,134 | 2/1940 | Garside et al. | 514/4 |
| 2,474,729 | 1/1946 | Durel et al. | 514/3 X |
| 2,538,018 | 1/1951 | Krayenbühl et al. | 514/4 X |
| 2,801,953 | 8/1957 | Dorzbach et al. | 514/4 |
| 3,856,771 | 12/1974 | Jackson | 530/303 |
| 3,868,358 | 2/1975 | Jackson | 530/303 |
| 3,903,069 | 9/1975 | Gregory et al. | 530/303 |
| 4,196,196 | 4/1980 | Tiholiz | 514/4 |
| 4,472,385 | 9/1984 | Brange et al. | 514/3 |
| 4,764,592 | 8/1988 | Massey et al. | 530/303 |
| 4,839,341 | 6/1989 | Massey et al. | 514/4 |

FOREIGN PATENT DOCUMENTS 63000 12/1944 Denmark.

Primary Examiner—Howard E. Schain
Assistant Examiner—Susan M. Perkins
Attorney, Agent, or Firm—Morris Fidelman; Franklin D. Wolffe

[57] ABSTRACT

Insulin preparations with improved properties for parenteral administration can be prepared at pH values of about 3 to 8.5 by presence of magnesium ions in concentration of about 0.005 to 0.5M, a preferred range is 0.02M to 0.5M.

12 Claims, No Drawings

MAGNESIUM CONTAINING INSULIN SOLUTION

This application is a continuation in part of Ser. No. 109,065 filed Oct. 16, 1987, now abandoned.

The present invention relates to insulin preparations containing magnesium ions. The preparations exhibit improved therapeutic properties.

Insulin preparations used for treatment of diabetics comprise both solutions and suspensions of insulin. The insulin suspensions, all with protracted action, have pH values around 7. The insulin solutions have pH values either around 3 (rapidly acting as well as protracted-acting solutions) or around 7 (rapidly acting solutions only).

The reason for the gap between the two pH intervals for insulin solutions is the low solubility in water of insulin around its isoelectric pH (approximately 5.3) both in the absence of zinc ions (Tanford and Epstein: J. Am. Chem. Soc. 76 (1954), 2163-69, FIG. 1) and in the presence of zinc ions (Fredericq and Neurath: J. Am. Chem. Soc. 72 (1950), 2684-91, FIG. 4).

The acid insulin solutions are now not so widely used as in the beginning of the insulin era, because of the degradation of insulin by deamidation.

The present invention is based on the following surprising findings:

1) Solutions containing insulin in therapeutically relevant concentrations can be prepared at magnesium ion concentrations of about 0.02 to 0.5 mol/liter in the pH range of about 4 to 6.2, i.e., at around the isoelectric point of insulin.

2) In the pH range of about 3-4, which is inappropriate for insulin because of chemical instability, useful solutions of insulin derivatives can be made in the presence of magnesium ions in concentrations of about 0.005 to 0.5M, provided that $Asn^{A21}$ is substituted by an amino acid residue not containing an amido group.

3) Also in the pH range of about 6.2-8.5, useful insulin solutions, optionally containing an insulin precipitate, can be made in the presence of magnesium ions in concentrations of about 0.005 to 0.5M.

The preparations of this invention have properties that are superior to the heretofore conventional insulin preparations.

As to 1) it has now surprisingly been found that many magnesium salts, for example magnesium chloride, have a solubilising effect on insulin at pH values of about 4 to 6.2, both per se and in comparison to the corresponding sodium, potassium and ammonium salts (see Example 1 below). Various mixtures of magnesium salts have the same effect. It is, therefore, concluded that the presence of magnesium ions at certain concentrations is a critical parameter for the solubility of insulin at pH values of about 4 to 6.2.

The term magnesium ions is intended herein to comprise both free and bound magnesium ions.

It was furthermore surprisingly found that protamine can be included in the insulin solutions of this invention having pH values of about 4 to 6.2 without precipitation of protamine-insulin complex. Upon adjustment to pH value of about 7, such a complex precipitates.

Calcium ions also increase insulin solubility in the pH range of about 4 to 6.2. However, the results of in vitro experiments under simulated physiological conditions indicate that injection of a solution containing calcium ions into tissue will cause precipitation of calcium carbonate and calcium phosphate even at calcium concentrations far below 0.05M. Other experiments indicate that precipitation of corresponding magnesium compounds will not take place upon injection of solutions according to this invention. As precipitation of calcium compounds in tissue may be harmful (because of the risk of artificial calcification) the content of free calcium ions in the insulin preparations of this invention should not be substantially higher than what corresponds to the calcium level in extracellular fluids. Preferably, the preparations of this invention contain less than about 10 mM calciums, more preferred less than about 2 mM calcium ions.

Insofar as the inventor hereof is aware, prior art teachings relating to insulin solutions containing magnesium ions do not contemplate the pH interval of pH 4 to 6.2, or magnesium ion concentrations of 0.005 to 0.5 mol/liter.

Danish patent specification No. 63,000 deals with preparations containing suspensions of complexes formed by insulin, protracting agents (i.e. protamine) and magnesium ions at pH values from 6.5 to 7, the magnesium concentrations disclosed are below 0.004M.

U.S. patent specification No. 4,196,196 relates to a composition for enhancing vascular perfusion and reperfusion in disease states, which composition consists of glucose, insulin and magnesium dipotassium ethylene diamine tetraacetic acid. According to the example, the known preparation contains 0.02 insulin units per ml.

U.S. patent specification No. 4,472,385 deals with stabilization of zinc insulin solutions at pH values from 7 to 8 and the improved stability is obtained by the addition of about 0.0004 to 0.01M calcium or magnesium ions. The upper limit of magnesium concentration in the known examples is 0.002M.

The matters of the three above noted patents are outside the scope of this invention.

According to this invention, magnesium ions in the above described concentration range may be added to a solution of insulin or of an insulin derivative which solution, if desired, furthermore contains precipitated insulin or a precipitated insulin derivative having protracted action. For the purpose of subcutaneous administration, magnesium ions are added in order to obtain a solution with a more rapid onset of action or, if the solution contains protamine, a protracted effect. If the composition of this invention also contains precipitated insulin or a precipitated insulin derivative, a biphasic preparation may be obtained. Compared with the known biphasic insulin preparations, the biphasic preparations according to this invention have a more rapid onset of blood sugar lowering effect. Examples of precipitated insulin are zinc insulin crystals and protamine zinc insulin crystals.

BRIEF STATEMENT OF THIS INVENTION

Thus, the present invention relates to insulin solutions, optionally containing an insulin precipitate, for parenteral administration having a pH value in the range of about 3 to 8.5 and containing magnesium ions in the concentration range from about 0.005 to 0.5 Molar, preferably 0.02M to 0.5 Molar.

The concentration of dissolved insulin may be in the range of about 20 to 500 insulin units per ml.

Known to the art stabilizers and preservatives may be present in the insulin preparation.

Protamine may be present, desirably as from 8 to 40% (weight/weight) based upon the weight of insulin, 10 to 30% (weight/weight) being a preferred range.

ATTRIBUTES OF THIS INVENTION

Absent retarding substances in the insulin solutions of this invention, the absorption of insulin was surprisingly found to be faster than that of the reference insulin (see Examples 2-9 and 11 below). This property is useful for a rapidly acting insulin, in particular in connection with a multiple injection regimen where insulin is given before each meal. With quicker onset of action, the insulin can conveniently be taken closer to the meal than with conventional rapidly acting insulin solutions. Furthermore, a faster disappearance of insulin probably diminishes the risk of post meal hypoglycemia.

Insulin solutions of this invention having a pH value in the range 3-6.2 may also be particularly useful for the purpose of infusion by means of pumps, because of a lack of insulin precipitation caused by carbon dioxide diffusion through catheters. Such precipitation has been observed occasionally with neutral infusion solutions, and is believed to be attributable to the lowering of the pH value caused by carbon dioxide.

Insulin solutions of this invention containing above about 5%, preferably above about 8%, more preferred above about 10% (weight/weight), protamine on the basis of insulin, exhibits a delayed absorption of insulin after subcutaneous injection into pigs as compared to the reference insulin (see Examples 4 and 5 below). Preferably, the content of protamine is below about 50%, preferably below about 40%, more preferred below about 30%, (weight/weight). Protamine insulin preparations of this invention have an advantage over protracted acting neutral insulin protamine suspensions because the inconvenience of sedimentation is lacking. The known neutral protamine insulin preparations are suspensions, whereas the preferred protamine insulin preparations of this invention are solutions at pH values of below about 6.2.

The solutions of this invention are believed to be particularly well suited for application in the fountain pen like devices used for multiple injection insulin therapy.

The preparations of this invention may contain a naturally occurring insulin and/or a derivative thereof. Preferred insulins for practice of this invention are human, porcine and bovine, most preferably human. Also, other naturally occurring insulins may be employed in practice of this invention. Preferably, insulin of high purity is used. Within the context of this invention, the term insulin when employed in a plural or generic sense is intended to encompass both naturally occurring insulins and insulin derivatives.

Some property differences can be expected to exist between the naturally occurring insulins and insulin derivatives.

Herein, the term derivatives of insulin (or insulin derivatives) is applied to peptides having blood sugar lowering effect and having an amino acid composition which is identical with that of human insulin with the proviso that a few of the amino acid residues are exchanged with other amino acid residues and, optionally, the C terminal carboxy group of the B chain is protected. Examples of such insulin derivatives are, inter alia, described in two European patent applications, publication Nos. 86301755 and 86306721, the content of which is hereby incorporated by reference.

When human, porcine or bovine insulin is used for solutions according to this invention, the zinc content of the insulin has to be low, preferably less than 0.1 zinc ions/hexamer (corresponding to less than 0.02% (weight/weight) on the basis of insulin), in order to avoid precipitation of insulin at the pH values above about 4, and this also applies for solutions containing protamine. Zinc insulin crystals can be freed of zinc, e.g. by a salting out procedure followed by precipitation at pH 5 (Schlichtkrull: Acta Chem. Scand. 10 (1956), 1455-58). However, if agents capable of forming complexes with zinc, such as citrate, are present the content of zinc may be higher.

When insulin derivatives are used, the zinc content may not be critical to the same extent. In some cases of insulin derivatives, a high level of zinc ions (e.g. up to 10 zinc ions/hexamer) may be compatible with insulin solubilities under the conditions of the solutions according to this invention, and may even be desirable (c.f. European patent application No. 86301755).

Protamine is known to be a heterogeneous mixture. Protamine can be obtained from fishes such as *Oncorhynchus keta*. However, also protamine from other fishes can be used. Normally, protamine is marketed as protamine sulphate. However, also other salts can be used. Preferably, protamine of high purity is used.

As examples of other preferred preparations of this invention, preparations containing both zinc and protamine can be mentioned. In such preparations, which may be solutions of insulin derivatives in the pH range of 3-4 or neutral suspensions of mammalian insulin, the content of zinc may be up to about 25 zinc ions per hexamer insulin or insulin derivative.

The content of insulin in solutions of this invention may be in the range of 20 to 500 IU/ml, preferably in the range of 40 to 100 IU/ml, in preparations for injection. However, for other purposes of parenteral administration, the insulin content may be higher. The insulin solution may be mixed with a solid insulin material such as zinc insulin crystals or zinc protamine insulin crystals.

According to this invention, a variety of soluble magnesium salts can be used, both separately and mixed. Examples of applicable anions are chloride, sulphate, monocarboxylates like acetate, propionate and butyrate, and dicarboxylates like succinate, aspartate and glutamate. The optimum concentration of magnesium ions will depend on the salt(s) applied and should be chosen with regard to requirements for the desired timing of the preparation, the insulin solubility and the proximity of the composition to isotonic conditions. Isotonic concentrations of magnesium salts show great variation as can be illustrated by the isotonic concentrations of magnesium chloride and magnesium sulphate being approximately 0.1M and 0.26M, respectively. Other salts, amino acids, and non-ionic agents (besides preservatives) may be present if they are non-toxic and compatible with the insulin preparation as a whole.

According to this invention, the range of applicable magnesium ion concentrations is about 0.005M to 0.5M, preferably about 0.02M to 0.5M, more preferably above 0.05M. The upper limit is somewhat arbitrary being chosen from the assumption that in some cases (e.g., for intraperitoneal infusion) some overstepping of isotonicity may be acceptable. According to a preferred embodiment of this invention, the preparations contain about 0.08M to 0.3M magnesium ions.

The preservative present in the insulin preparation of this invention may be as in the heretofore conventional insulin preparations, for example phenol, m-cresol and methylparaben.

For preparation of aqueous insulin solutions according to this invention, a slightly acidic solution of insulin can be mixed with a solution containing all the other components of the final preparation. Then follows adjustment of pH value if required, stirring until a clear solution is obtained and finally sterile filtration. If desired, a sterile, protracted-acting insulin suspension may be added to the sterile insulin solution yielding a preparation with biphasic action. In order to protect the preparations from the denaturation that may take place by occasional heating and shaking, known stabilising agents, such as phospholipids, may be included.

Preparations containing an insulin derivative are prepared analogously.

The insulin preparations of this invention can be used in the treatment of diabetics. It is recommended that the dosage of the insulin preparations of this invention be selected by a physician similarly to the selection of the dosage of known insulin preparations for injection.

The following examples illustrate how magnesium ions increase the solubility of insulin, how preferred insulin preparations of this invention can be prepared and how they act after injection into pigs.

EXAMPLE 1

Acid solutions containing 200 IU zinc free human monocomponent insulin per ml, a trace amount of human mono-$^{125}$I-(A19)-insulin, 2 g phenol/liter and a salt (listed in Table I below) at approximately isotonic concentration were adjusted to the pH values listed in Table I. The solubilities were determined by measurement of radioactivity concentrations in the supernatants and conversion of the results to IU/ml (1 IU corresponds to 38 μg of insulin). The effect of the salts on solubility of insulin (IU/ml) at room temperature may be seen in Table I.

TABLE I

| pH | 0.1M MgCl$_2$ | 0.15M NaCl | 0.15M KCl | 0.15M NH$_4$Cl |
| --- | --- | --- | --- | --- |
| 3.5 | above 200 | above 200 | above 200 | above 200 |
| 4.0 | 135 | 79 | 98 | 109 |
| 4.5 | 85 | 20 | 26 | 29 |
| 5.0 | 104 | 16 | 17 | 22 |
| 5.5 | 124 | 18 | 21 | 25 |
| 6.0 | 70 | 25 | 32 | 29 |
| 6.5 | 21 | 41 | 56 | 27 |

Table I shows that solubility of the insulin in an approximately isotonic solution of magnesium chloride is surprisingly much higher than the solubilities in corresponding solutions of sodium chloride, potassium chloride and ammonium chloride all at pH 4-6, and approaches 100 IU/ml, a commonly used concentration in insulin preparations for injection.

The solubility of insulin (IU/ml) at room temperature, at pH 5.5 and at different concentrations of the salts were determined and appear in Table II below.

TABLE II

| Salt conc. M | MgCl$_2$ | NaCl | KCl | NH$_4$Cl |
| --- | --- | --- | --- | --- |
| 0.025 | 12 | 4 | 4 | 5 |
| 0.050 | 33 | 5 | 6 | 5 |
| 0.075 | 72 | 7 | 9 | 8 |
| 0.10 | 101 | 11 | 12 | 11 |
| 0.15 | above 200 | 21 | 21 | 25 |
| 0.20 | above 200 | 37 | 34 | 39 |
| 0.25 | above 200 | 41 | 54 | 66 |
| 0.30 | above 200 | 76 | 74 | 108 |
| 0.35 | above 200 | 69 | 84 | 123 |
| 0.40 | above 200 | 100 | 119 | 146 |

Table II evidences a superior solubility in magnesium chloride solutions compared to sodium chloride, potassium chloride and ammonium chloride solutions over a wide range of salt concentrations.

EXAMPLE 2

A solution, designated 1, with the following composition was prepared: 0.15M magnesium butyrate, 0.006M citric acid, 2 g/liter phenol and 100 IU/ml zinc free human monocomponent insulin; pH: 5.8.

A solution, designated 0, made as a standard rapidly acting insulin preparation, Actrapid ™ HM, with the following composition, was used as reference: 16 g glycerol/liter, 2 g phenol/liter and 100 IU/ml of human monocomponent insulin (2 zinc ions/hexamer); pH: 7.4. The medium complies with the requirements of United States Pharmacopeia XIX for Neutral Insulin Injection.

Human mono-$^{125}$I-(A19)-insulin was added in trace concentrations (0.3-1 μCi/ml) to both solutions. Then, 0.1 ml of each solution was separately injected subcutaneously into two pigs. The absorption was followed by external monitoring of the radioactivity remaining at the site of injection by means of a scintillation crystal detector, coupled to a spectrometer, in analogy to a method developed for absorption studies in humans (Binder (1969): "Absorption of injected insulin". Thesis). Blood samples were taken for determination of plasma glucose and plasma insulin. The results are shown in Table III below.

Table III shows the time courses of residual radioactivity, plasma glucose and plasma IRI (immuno-reactive insulin, determined by radioimmunoassay). The amounts of radioactivity at the site of injection are given in percents of the amount measured immediately after injection (time=0). Plasma glucose concentrations are given in percents of the value for the blood sample taken immediately before injection (time=0).

Solution 0: Reference solution given in one pig (weight: 77 kg).

Solution 1: Test solution given in another pig (weight: 79 kg).

TABLE III

| Time after injection min. | % Radioactivity | | % Plasma glucose | | Plasma IRI. μU/ml | |
| --- | --- | --- | --- | --- | --- | --- |
| | 0 | 1 | 0 | 1 | 0 | 1 |
| −15 | — | — | 98 | 98 | below 5 | below 5 |
| 0 | 100 | 100 | 100 | 100 | below 5 | below 5 |
| 30 | 91 | 67 | 95 | 41 | 16 | 25 |
| 60 | 76 | 54 | 67 | 49 | 18 | 23 |
| 90 | 69 | 40 | 56 | 43 | 19 | 18 |
| 120 | 56 | 27 | 51 | 41 | 13 | 14 |
| 180 | 38 | 11 | 47 | 45 | 10 | 5 |
| 240 | 23 | 5 | 58 | 78 | 9 | below 5 |
| 300 | 14 | 3 | 65 | 108 | 7 | below 5 |

As may be seen from Table III, the test insulin is absorbed faster than the reference insulin. This is in complete agreement with the relationships between the time courses of percentage plasma glucose for the solutions 0 and 1, and between the time courses of plasma IRI for the solutions 0 and 1, respectively.

EXAMPLE 3

A solution designated 2 with the following composition was prepared: 0.175M magnesium acetate, 0.0375M acetic acid, 2 g/liter phenol, 100 IU/ml zinc free human monocomponent insulin; pH 5.5.

Tracer insulin was added as in Example 2. 0.1 ml of solution 2 was injected subcutaneously into one pig at one side of the neck, whereas 0.1 ml of reference insulin solution, 0, (prepared as described in Example 2) was injected subcutaneously into the same pig at the other side of the neck. The absorption was followed as in Example 2. One week after, the experiment was repeated with crossing over between injection sites. The results are shown in Table IV.

TABLE IV

Time course of % residual radioactivity. Mean values from two experiments in the same pig.

| Time after injection min. | % Radioactivity | |
|---|---|---|
| | 0 | 2 |
| 0 | 100 | 100 |
| 30 | 92 | 79 |
| 60 | 86 | 63 |
| 90 | 73 | 53 |
| 120 | 63 | 44 |
| 180 | 42 | 26 |
| 240 | 25 | 12 |
| 300 | 15 | 5 |

It appears from this table that the test insulin is absorbed faster than the reference insulin.

EXAMPLE 4

Two solutions designated 3A and 3B with the following compositions were prepared: 3A: 0.14M $MgSO_4$, 0.05M $MgCl_2$, 2 g/liter phenol, 100 IU/ml zinc free human monocomponent insulin; pH adjusted to 5.5 with HCl. 3B: As 3A, but with an addition of 1 mg protamine sulphate/ml.

Tracer insulin was added as in Example 2. 0.1 ml of solution 3A was injected subcutaneously into Pig I and Pig II at one side of the neck. 0.1 ml of solution 3B was injected correspondingly in Pig III and Pig IV. 0.1 ml of a reference insulin solution, 0, (prepared as described in Example 2) was injected subcutaneously into each of the four pigs at the other side of the neck. The absorption was followed as in Example 2. The results are shown in Table V.

TABLE V

Time courses of residual radioactivity. 3A: without protamine. 3B: with protamine.

| Time after injection min. | % Radioactivity | | | | | | | |
|---|---|---|---|---|---|---|---|---|
| | Pig I | | Pig II | | Pig III | | Pig IV | |
| | 0 | 3A | 0 | 3A | 0 | 3B | 0 | 3B |
| 0 | 100 | 100 | 100 | 100 | 100 | 100 | 100 | 100 |
| 30 | 97 | 89 | 85 | 79 | 92 | 103 | 94 | 95 |
| 60 | 89 | 69 | 75 | 54 | 77 | 93 | 78 | 93 |
| 90 | 71 | 63 | 62 | 43 | 60 | 95 | 65 | 88 |
| 120 | 66 | 45 | 54 | 29 | 50 | 86 | 53 | 82 |
| 180 | 45 | 25 | 38 | 13 | 30 | 82 | 34 | 73 |
| 240 | 26 | 12 | 24 | 6 | 15 | 83 | 18 | 71 |
| 300 | 16 | 6 | 17 | 3 | 9 | 73 | 11 | 66 |

It appears from this table that the test insulin is absorbed faster than the reference insulin in the absence of protamine, but more slowly than the reference insulin in the presence of protamine.

EXAMPLE 5

Three solutions designated 4A, 4B and 4C with the following compositions were prepared: 4A: 0.18M magnesium succinate, 0.01M $MgCl_2$, 0.002M $MnSO_4$, 0.02M succinic acid, 2 g/liter phenol, 100 IU/ml zinc free human monocomponent insulin; pH 5.6. 4B: As 4A but with an addition of 0.55 mg protamine sulphate/ml. 4C: As 4A but with an addition of 0.73 mg protamine sulphate/ml.

Tracer insulin was added as in Example 2. 0.1 ml of solutions 4A, 4B and 4C was injected subcutaneously into Pigs A, B and C, respectively, at one side of the neck. 0.1 ml of a reference insulin solution, 0, (prepared as described in Example 2) was injected subcutaneously into each of the three pigs at the other side of the neck. The absorption was followed as in Example 2. One week after, the experiment was repeated with crossing over between injection sites. The results are shown in Table VI.

TABLE VI

Data from Example 5. Time courses of residual radioactivity. Mean values from two experiments. 4A: without protamine. 4B: with protamine, low content. 4C: with protamine, high content.

| Time after injection min. | % Radioactivity | | | | | |
|---|---|---|---|---|---|---|
| | Pig A | | Pig B | | Pig C | |
| | 0 | 4A | 0 | 4B | 0 | 4C |
| 0 | 100 | 100 | 100 | 100 | 100 | 100 |
| 30 | 91 | 82 | 92 | 87 | 92 | 89 |
| 60 | 78 | 71 | 87 | 86 | 84 | 87 |
| 90 | 66 | 57 | 74 | 80 | 71 | 85 |
| 120 | 51 | 45 | 63 | 73 | 59 | 81 |
| 180 | 33 | 23 | 47 | 62 | 40 | 70 |
| 240 | 21 | 15 | 35 | 54 | 25 | 66 |
| 300 | 15 | 9 | 25 | 46 | 17 | 56 |
| 480 | 10 | 6 | 16 | 35 | 9 | 45 |
| 600 | 8 | 4 | 8 | 27 | 5 | 31 |
| 720 | 6 | 4 | 5 | 17 | 4 | 19 |

It appears from this table that relative to the reference insulin the test insulin is absorbed faster in the absence of protamine, more slowly with the low content of protamine and yet more slowly with the high content of protamine.

In Examples 6 to 8, 10 and 11 the absorption properties of the test preparations were examined in comparison to a human Actrapid reference solution, as in Examples 2–5. In Example 9 another reference solution was used, see below. For the sake of simplification, however, the result of the comparison is given as the average ratio:

$$R = T_{50\%}(\text{test})/T_{50\%}(\text{ref})$$

where $T_{50\%}(\text{test})$ and $T_{50\%}(\text{ref})$ is the time elapsing from the time of injection until the radioactivity measured at the site of injection has decreased to the half of the initial value for test and reference, respectively. The number of pigs involved is designated N.

EXAMPLE 6

Test solution: 0.14M $MgSO_4$, 0.05M $MgCl_2$, 0.01M magnesium acetate, 0.002M $CaCl_2$, 2 g m-cresol/l, 100 IU/ml zinc free human monocomponent insulin plus human tracer insulin; pH value adjusted to 5.7 with hydrochloric acid.

0.04 ml of each of the test and reference solutions was injected into each pig.

The R-value was found to be 0.73 (N=6).

EXAMPLE 7

Test solution: 0.02M $MgCl_2$, 0.11M arginine monohydrochloride, 2 g phenol/l, 100 IU/ml zinc free human monocomponent insulin plus tracer insulin; pH value adjusted to 7.7 with NaOH.

0.08 ml of each of the test and reference solutions was injected to each pig.

The R-value was found to be 0.74 (N=2).

EXAMPLE 8

Test solution: 0.095M $MgCl_2$, 2 g phenol/l, 100 IU equivalents/ml zinc free porcine monodesamidoinsulin plus tracer derivative; pH value adjusted to 3.2 with hydrochloric acid.

0.08 ml of each of the test and reference solutions was injected into each pig.

The R-value was found to be 0.71 (N=2).

EXAMPLE 9

Test solution: 0.095M $MgCl_2$, 2 g phenol/l, 100 IU equivalents/ml zinc free human insulin derivative with Ser(B9) substituted by Asp and Thr(B27) substituted by Glu, plus tracer derivative; pH value adjusted to 7.4.

As the derivative, formulated as Actrapid, was known beforehand to be more quickly absorbed than human Actrapid (cf. European patent application No. 83306721), the reference solution in this Example was the derivative formulated as Actrapid and with 100 IU equivalents/ml derivative.

0.08 ml of each of the test and reference solutions was injected into each pig.

The R-value was found to be 0.85 (N=5).

Thus also with this more quickly absorbable insulin derivative, an enhancing effect on the absorption is mediated by magnesium ions.

EXAMPLE 10

Test solution 1: 0.095M $MgCl_2$, 0.002M zinc acetate, 1 mg protamine sulphate/ml, 3 g m-cresol/ml, 100 IU equivalents/ml zinc free porcine monodesamidoinsulin plus tracer derivative; pH value adjusted to 3.2 with hydrochloric acid.

Test solution 2: as 1, except that 0.095M $MgCl_2$ was substituted by 0.14M NaCl.

0.05 ml of the test solution (either 1 or 2) and of the reference solution (human Actrapid® plus human tracer insulin) was injected into each pig.

The R-values were found to be 3.7 (N=2) and 2.9 (N=2) for test solutions 1 and 2, respectively.

The results demonstrate the protracting effect of magnesium ions, in addition to that of zinc ions, for protamine containing monodesamidoinsulin solutions.

EXAMPLE 11

A pharmacokinetic investigation was performed in healthy volunteers. Test solution: 0.14M $MgSO_4$, 0.05M $MgCl_2$, 0.01M magnesium acetate, 2 g m-cresol/l, 100 IU/ml zinc free human monocomponent insulin; pH value adjusted to 5.7 with hydrochloric acid. Reference solution (Actrapid ™ HM): 16 g glycerol/l, 3 g m-cresol/l, 100 IU/ml human monocomponent insulin (3 zinc ions/hexamer); pH: 7.4.

Human $^{125}I$-insulin was added in trace concentrations of 5 and 3 μCi/ml to the test and reference solution, respectively. 4 IU of the test solution was injected subcutaneously on one thigh and 4 IU of the reference solution on the other thigh of each person. The allocation of the two preparations between left and right thigh was randomized. The absorption was followed by continuous external monitering of the radioactivity remaining at the site of injection on each thigh.

The R-value was found to be 0.78 (N=15). Thus, absent retarding substances, an enhancing effect on the absorption of insulin is also mediated by magnesium ions in humans.

EXAMPLE 12

A solution with the following composition is made: 50 IU/ml zinc free human monocomponent insulin, 0.005M $MgCl_2$, 2 g m-cresol/l; pH adjusted to 8.5.

EXAMPLE 13

A solution with the following composition is made: 50 IU/ml zinc free human monocomponent insulin, 0.5M $MgCl_2$, 2 g m-cresol/l; pH adjusted to 5.8.

EXAMPLE 14

This example is a comparison between a solution (A) according to the present invention and a solution (B) according to U.S. patent specification No. 4,472,385, Example 8, except that porcine insulin was substituted by human insulin.

Solution A: 0.24M $MgSO_4$, 0.03M magnesium succinate, 2 g phenol/l, 100 IU/ml zinc free human monocomponent insulin containing a trace of human $^{125}I$-insulin; pH 6.1.

Solution B: 0.002M $MgCl_2$, 16 g glycerol/l, 2 g phenol/l, 100 IU/ml human monocomponent insulin containing 0.4% zinc and a trace of human $^{125}I$-insulin; pH 7.5.

4 IU of solution A was injected subcutaneously at one side of the neck in 6 pigs and 4 IU of solution B at the other side in the same 6 pigs.

The mean values of $T_{50\%}$ (see Example 5) was found to be 1.17 and 1.58 for solutions A and B, respectively, corresponding to a ratio of 0.74.

Hence this example proves that the preparation according to the present invention has a surprisingly more rapid action than the known preparation.

The features disclosed in the foregoing description and in the following claims may, both separately and in any combination thereof, be material for realizing this invention in diverse forms thereof.

I claim:

1. Insulin preparations for parenteral administration containing at least 20 insulin units per ml, comprising a solution of an insulin and magnesium ions in a magnesium concentration in the range from about 0.02 to 0.5M, the preparation having a pH value in the range from about 3 to 8.5.

2. Preparation, according to claim 1, characterized in that it has a pH value in the range from about 4 to about 6.2.

3. Preparation, according to claim 2, characterized in that the pH value is in the range from about 5 to 6.

4. Preparation, according to claim 1, characterized in that the magnesium concentration is in the range from 0.02M to 0.3M.

5. Preparation, according to claim 4, characterized in that the magnesium concentration is in the range of 0.08M to 0.3M.

6. Preparation, according to claim 1, characterized in that it has an activity in the range from about 30 to 500 insulin units per ml.

7. Preparation, according to claim 6, characterized in that it has an activity in the range from about 40 to 100 insulin units per ml.

8. Preparation, according to claim 1, characterized in that it contains protamine.

9. Solution, according to claim 8, characterized in that it contains about 5% to 50% (weight/weight) of protamine based upon the content of insulin, with the proviso that the pH value is below 6.2.

10. Preparation, according to claim 1, characterized in that it contains less than about 1 zinc ion per hexamer insulin.

11. Process of preparing insulin solutions for parenteral administration which comprises mixing a water soluble magnesium salt, an insulin and water, the magnesium concentration being in the range from about 0.02M to 0.5M, the insulin concentration being in the range from about 20 to 500 insulin units per ml, the pH being adjusted to a level in the range from about 3 to 8.5.

12. Process according to claim 11 further comprising a magnesium concentration range from 0.08M to 0.3M, an insulin concentration range from 40 to 100 insulin units per ml and a pH in the range from about 5 to 6.

* * * * *